United States Patent [19]

Burnham et al.

[11] Patent Number: 5,486,459
[45] Date of Patent: Jan. 23, 1996

[54] BIOLOGICALLY RELEVANT METHODS FOR THE RAPID DETERMINATION OF STERILITY

[75] Inventors: Jeffrey C. Burnham; George J. Hageage; Douglas Jambard-Sweet, all of Maumee; Judy Hendricks, Findlay, all of Ohio

[73] Assignee: Medical College of Ohio, Toledo, Ohio

[21] Appl. No.: 380,195

[22] Filed: Jan. 30, 1995

Related U.S. Application Data

[63] Continuation of Ser. No. 126,197, Sep. 24, 1993, abandoned, which is a continuation-in-part of Ser. No. 970,307, Nov. 2, 1992, abandoned, which is a continuation-in-part of Ser. No. 859,066, Mar. 27, 1992, abandoned, which is a continuation-in-part of Ser. No. 450,394, Dec. 14, 1989, abandoned.

[51] Int. Cl.$^6$ .............................. C12Q 1/22; G01N 21/00
[52] U.S. Cl. .................. 435/31; 435/4; 435/25; 435/26; 435/29; 435/287.4; 435/810; 435/832; 435/842; 435/920; 422/58; 422/61; 422/86; 422/88; 422/102; 206/528; 206/530; 206/534
[58] Field of Search ..................... 435/31, 4, 25, 435/26, 29, 287, 288, 291, 810, 832, 842, 920; 422/58, 61, 86, 88, 102; 206/528, 530, 534

[56] References Cited

U.S. PATENT DOCUMENTS

| | | | |
|---|---|---|---|
| 2,606,654 | 4/1945 | Davis et al. | 435/31 |
| 3,239,429 | 2/1963 | Menolasino et al. | 435/31 |
| 3,440,144 | 5/1965 | Andersen | 435/31 |
| 3,981,683 | 9/1976 | Larsson et al. | 435/31 |
| 4,001,587 | 1/1977 | Panchenkov et al. | 435/31 |
| 4,038,873 | 8/1977 | Kimmel | 435/31 |
| 4,155,895 | 5/1979 | Rohowetz et al. | 422/57 |
| 4,388,233 | 6/1983 | Bissell et al. | 435/31 |
| 4,448,548 | 5/1984 | Foley | 435/31 |
| 4,596,773 | 6/1986 | Wheeler, Jr. | 435/31 |
| 4,663,287 | 5/1987 | Barker | 435/188 |
| 4,717,661 | 1/1988 | McCormick et al. | 435/31 |
| 4,732,850 | 3/1988 | Brown et al. | 435/31 |
| 4,741,437 | 5/1988 | Gorski et al. | 435/31 |
| 4,885,253 | 12/1989 | Kralovic | 435/296 |
| 5,073,488 | 12/1991 | Matner et al. | 435/31 |
| 5,167,923 | 12/1992 | Van Iperen | 422/58 |
| 5,223,401 | 6/1993 | Foltz et al. | 435/31 |
| 5,252,484 | 10/1993 | Matner et al. | 435/288 |

*Primary Examiner*—Michael G. Wityshyn
*Assistant Examiner*—Abdel A. Mohamed
*Attorney, Agent, or Firm*—Baker & Botts; James Remenick

[57] ABSTRACT

The invention is directed to biological processes and apparatus for determining the efficacy of a sterilization cycle based upon the recovery of activity of interactive enzyme systems comprising enzymes, coenzymes, catalysts, cofactors, substrates or any other necessary reagents. The invention provides a vital process for expediting sterility verification before utilization of the articles thought to be sterilized. The invention involves the rapid detection of any surviving interactive enzymatic activity which directly relates to the probability of any biological spores surviving in a test sample. An absence of a change indicates that the sterilization process had inactivated the enzyme system thereby preventing the interactive reaction from taking place which is a rapid equivalent to directly detecting the survivability of bacterial spores in a similar test. The methods and apparatus of the invention are useful in the health care industry such as in hospitals, laboratories, and research institutions, in food and environmental technology, and in all technologies which utilize sterilization in manufacturing, production or waste disposal.

29 Claims, 10 Drawing Sheets

DIAGRAM OF INDICATOR VIAL CONSTRUCTION

COMPONENTS                    COMPLETED SYSTEM

OPERATION OF THE INDICATOR

1. Cap with sponge is removed.
2. Add indicator solution using eyedropper.
3. Incubate for specified time.
4. Disks are evaluated as a positive or negative result.

| AUTOCLAVING | | RELATIVE COLOR INTENSITY ON DISK |
|---|---|---|
| NONE | | 84+/-9 |
| 5 MINUTES |  | 74+/-11 |
| 15 MINUTES | | 2+/-0 |

— ● — SURVIVING SPORE POPULATION
---△--- ENZYME INDICATOR (400 ul OIL CONFIGURATION)
---▽--- ENZYME INDICATOR (200 ul OIL CONFIGURATION)
····◇···· ENZYME INDICATOR (100 ul OIL CONFIGURATION)

Layered solid support construct

BIOLOGICALLY RELEVANT METHODS FOR THE RAPID DETERMINATION OF STERILITY

REFERENCE TO RELATED APPLICATIONS

This application is a continuation of application Ser. No. 08/126,197, filed Sep. 24, 1993 now abandoned, which is a continuation-in-part of U.S. patent application Ser. No. 07/970,307, filed Nov. 2, 1992, now abandoned, which is a continuation-in-pan of U.S. patent application Ser. No. 07/859,066, filed Mar. 27, 1992, now abandoned, which is a continuation-in-part of now abandoned U.S. patent application Ser. No. 07/450,394, filed Dec. 14, 1989.

BACKGROUND OF THE INVENTION

1. Field of the Invention

The invention relates to methods for the rapid determination of the effectiveness of sterilization processes using indicators containing biologically relevant materials which are functionally comparable to, but are not, living microorganisms. Methods and apparatus of the invention are useful in the health care industry such as in hospitals, laboratories, and research institutions, in food and environmental technology, and in all technologies which utilize sterilization in manufacturing, production or waste disposal.

2. Description of the Background

Primarily in the health care industry, but also in many other industrial applications, it is nearly always necessary to monitor the effectiveness of the processes used to sterilize equipment such as medical devices, instruments and other nondisposable articles. In these settings, sterilization is generally defined as the process of completely destroying all viable microorganisms including structures such as viruses and spores. Standard practice in these hospitals is to include a sterility indicator in the batch of articles to be sterilized. The use of sterility indicators allows a direct and sensitive approach to assay the lethality of the sterilization process.

A standard type of biological sterility indicator includes a known quantity of test microbial spores. This indicator is placed into the sterilization chamber and exposed to the sterilization process along with the objects to be sterilized. The test microorganisms, for example *Bacillus stearothermophilus* or *B. subtilis* spores, are then incubated for a specified period of time under conditions which favor proliferation and examined for possible growth, as determined by the presence or absence of certain metabolic products, of any surviving microorganisms. Positive growth indicates that the sterilization process was insufficient to destroy all of the microorganisms. While the apparatus for containing the spores has varied continuously, the general sterility detection process has not. Variations of this theme are disclosed in U.S. Pat. No. 3,239,429, 3,440,144, 4,596,773, 4,717,661, 4,732,850, and 5,167,923, which are hereby specifically incorporated by reference.

The biological indicators disclosed in each of these patents contain a preparation of viable spores made from a culture derived from a specific bacterial strain and characterized for predictable resistance to sterilization. Spores are often the test organism in conventional biological indicators because they are much more resistant to the sterilization process than most other organisms. The indicators are self-contained, meaning that they possess the spores and the incubation media in a single container. No additions are necessary to perform the test. Following sterilization, the ampule containing the incubation media is crushed to place the spores in contact with the growth media. The entire container is then incubated for a specified time and the results determined and recorded.

Although most indicators have been developed subsequent to 1975 and the enactment of the Medical Devices Act, there are also biological indicators which are on the market today that were developed prior to 1976 and thus, not governed by the requirements of the Act. These biological indicators are comprised of spores on a carrier in a package. After being exposed to the sterilization process, the carrier with the spores is transferred from the package to sterile media and incubated.

A major drawback of all these sterility indicators is the time delay in obtaining results of the sterility test. These sterility indicators normally require that the microorganisms be cultured for at least two and often up to seven days to assure adequate detection of any surviving microorganisms. During this time, the items which went through the sterilization process, should not be used until the results of the spore viability test have been determined. A viable spore result indicates that proper sterilization conditions were not met.

Many health care facilities have limited resources and must reuse their "sterilized" instruments within 24–48 hours and often immediately. In such settings, the seven day holding period for sterility verification is impractical and inefficient. The FDA Center for Devices and Radiological Health (CDRH) does permit incubations of less than seven days for new medical devices used by the health care facilities, provided that the manufacturer validates the shorter incubation parameters. For CDRH validation of incubation time, a partial cycle is needed which yields between 30 and 80% positives (survivors). A partial or incomplete sterilization cycle is an exposure to sterilant which is inadequate or unsuccessful in the destruction of microorganisms. The time when 97% of those positives showed growth is the acceptable incubation time. Using these guidelines it has not previously been possible for manufacturers to achieve a reduction in the holding period to less than 2 days.

There are even further time delays necessitated by these traditional commercial biological indicators because technicians must be trained and clean room facilities must be made available. In some cases it is necessary for the skilled laboratory technicians to transfer the test microorganisms from the sterility indicator packaging to the incubation media and to thereafter use their trained eye to check the incubation media for possible growth of microorganisms. Despite the use of trained technicians and other such precautions, on occasion the tests produce false positive results due to human error or contaminated clean room facilities. As a consequence, the articles must be re-sterilized which causes further delays and increased costs.

Certain industry standards should be followed to insure the effectiveness of the sterility indicator. These standards relate to the sensitivity and form of the microorganism employed, such as a spore, for the specific sterilization process. Product uniformity to assure consistent performance from one lot to the next is very important. Another important factor is the natural bioburden, the number of microorganisms on or in the product to be sterilized. The challenge to the sterilization process exceeds the challenge of the natural bioburden when the biological indicator is used within its performance characteristics. In order to meet these industry standards, some of the presently available sterility indicators require complicated handling techniques in addition to lengthy incubation periods.

The use of an enzyme and its subsequent activity as an indicator in an attempt to overcome the time delay in detecting sterility has recently been described in U.S. Pat. No. 5,073,488, which is hereby specifically incorporated by reference. The technique involves subjecting an enzyme to a sterilization cycle. Following the completion of the sterilization cycle, the enzyme is incubated with a substrate which is acted upon by the enzymes and transformed into a detectable product. The detection of the enzyme-modified product is performed either colorimetrically or fluorometrically. Disadvantages associated with this method are that only one enzyme was used in the sterility assay. Although 5,073,488 does state that the use of multiple enzymes is contemplated, each enzyme would be measured in isolation and they are not necessarily interactive or even functionally related. There was no rational for using a complex biological interaction to mimic the behavior of viable spores or that the enzyme reaction could be amplified to show a positive reaction much faster than by traditional enzymology would indicate. Specialized equipment was also often necessary to detect the product made by the single enzyme.

SUMMARY OF THE INVENTION

The invention provides methods and apparatus for determining the efficacy of a sterilization cycle based upon the activity of multiply interactive microbially-derived enzymes. Using these methods, sterility verification is very rapidly achieved. The invention combines the reliability of conventional biological indicators with the speed of techniques closer to that utilized by other enzymatic and chemical indicators, and allows for the utilization of personnel with minimal training while still achieving consistent and reliable results.

One embodiment of the invention is directed to a biological process for determining the effectiveness of a sterilization procedure, which may be microorganism-free. The process comprises the steps of placing a test indicator containing components of an interactive enzyme system into a sterilization chamber, performing the sterilization procedure within the chamber, adding any remaining components of the system to the previously added components to form a mixture, incubating the mixture for a period of time sufficient to form a product, and detecting the product to determine the effectiveness of the sterilization procedure. According to this method, the biological interaction will only occur if the components subjected to the sterilization process have not been destroyed or in some way inactivated. Components include the enzymes themselves, the substrates for the enzymes and any necessary coenzymes, catalysts, cofactors or other reagents of the enzyme system. The relationship between the components of the enzyme system is very relevant to a determination of sterility because it is not simply a chemical or enzyme reaction, but an enzyme interaction reflective of the physiological state of the microorganisms within the chamber. This degree of correlation is very high and of a fundamentally distinct nature than that provided with current methodologies.

Another embodiment of the invention is directed to a biological process for determining the effectiveness of a sterilization procedure as described above wherein the interactive enzyme system comprises an enzyme cycle such as a futile cycle, a substrate cycle, a galactosidase cycle, a citric acid cycle or the tricarboxylic acid cycle, a malate/isocitrate cycle, a coupled oxidation-reduction cycle such as the conversion of alpha-ketoglutarate to glutamate and phosphogluconate, cyclic phosphorylation, glycolysis including the kinase phosphatase cycles, or a combination thereof. According to this method, one or more components of the biological cycle are subjected to the sterilization process after which, the remaining components of the cycle are added to initiate the cycle. Inactivation of any single component inhibits completion of the cycle and creation of any significant amount of product, thereby indicating that the sterilization process was successfully completed.

Another embodiment of the invention is directed to a biological process for determining the effectiveness of a sterilization procedure as described above wherein the interactive enzyme system comprises an enzyme amplification system such as a fibrin/coagulation cascade, a complement cascade, a trypsin/trypsinogen cascade, or a combination thereof. The enzymes themselves are linearly or logarithmically amplified upon incubation with substrate, thereby producing a rapid build-up of enzyme modified substrate, or product, which is easily detected.

Another embodiment of the invention is directed to a two-step process for determining the effectiveness of a sterilization procedure. A test indicator containing one or more components of an interactive enzyme system, which may be a cycling or amplification system, and a culture of microorganisms are placed into a sterilization chamber. The sterilization procedure is performed within the chamber, after which the test indicator is removed. The remaining components of the system are added to treated components to form a mixture and a fluid media is added to the microorganisms to form a culture. The mixture is incubated for a first period of time sufficient to produce a detectable product and the product, if any, subsequently detected to make a first determination of the effectiveness of the sterilization procedure. The culture is incubated for a second period of time to produce a detectable metabolic product of growth and the product, if any, detected to make a second determination of the effectiveness of the sterilization procedure. In this two-step process, a very rapid initial determination of sterility can be made followed by a further second-step check involving actual culturing of the sterilization treated, biologically relevant microorganisms themselves.

Another embodiment of the invention is directed to a test indicator for determining the effectiveness of a sterilization procedure comprising an outer container having liquid impermeable and substantially gas non-absorptive walls, at least one opening covered with a gas-transmissive cover, said opening leading into a chamber which contains one or more components of an interactive enzyme system and a liquid impermeable or liquid semi-permeable barrier between the components and the opening. These components may be fixed to a solid support or free-floating in a non-aqueous or partially-aqueous solution. Test indicators may be entirely self-contained wherein after sterilization, the user simply causes the two vials within the indicator, one containing some components and the other the remaining components of the enzyme system, to mix their contents. If any enzyme activity is present, the enzymes plus any necessary coenzymes, cofactors and catalysts will interact with the substrate forming detectable product which can be assayed to determine the effectiveness of the sterilization procedure.

Other embodiments and advantages of the invention are set forth in part in the description which follows, and in part, will be obvious from this description, or may be learned from the practice of the invention.

DESCRIPTION OF THE INVENTION

Figure 1:
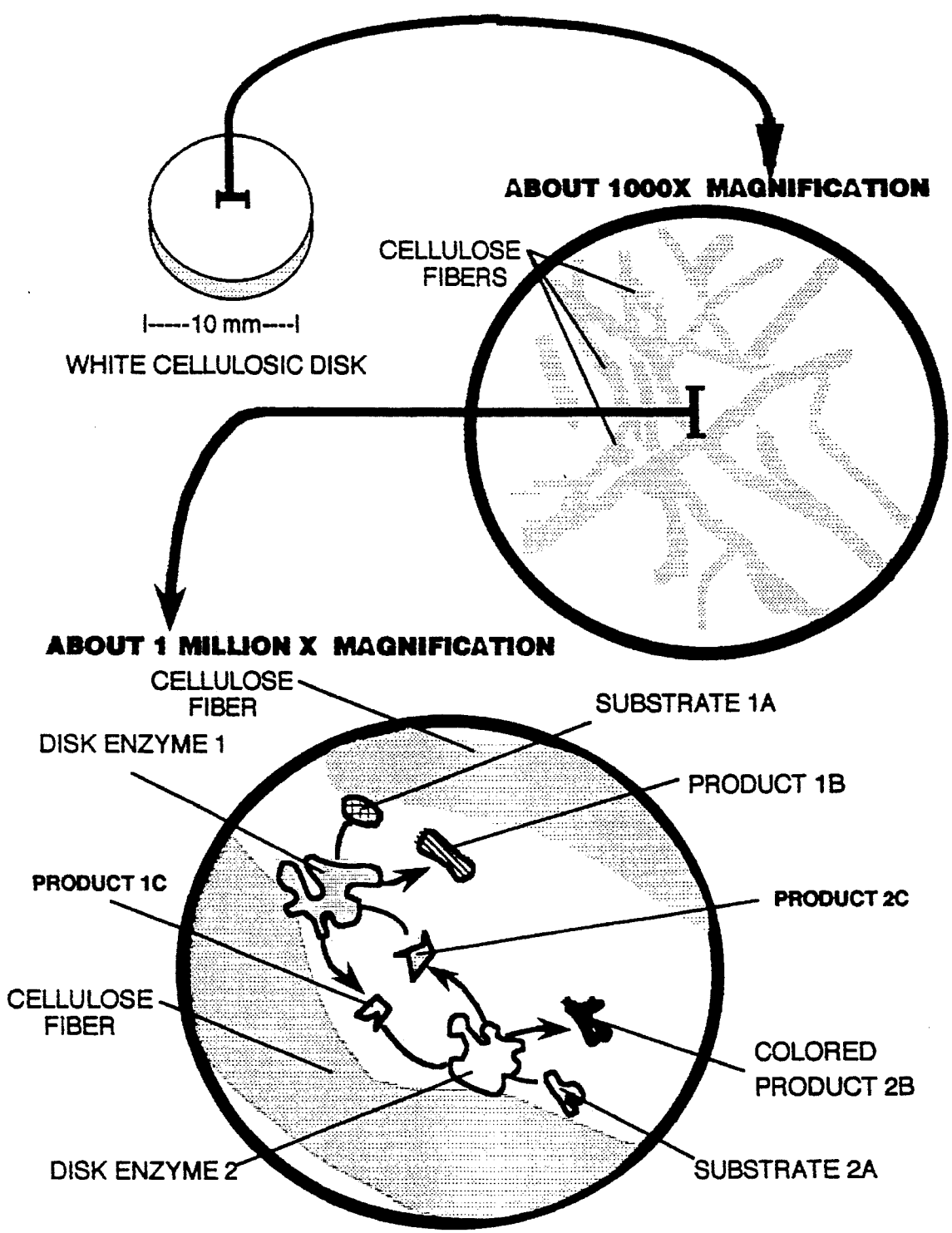
FIG. 1. Genetic schematic of the enzyme interaction and color development on a cellulosic disk.

The invention overcomes the problems and disadvantages associated with current strategies and designs and provides new methods and apparatus for the determination of microbial sterility. Living organisms such as bacterial spores have generally been used as indicators to test sterilization procedures to show that conditions were sufficient to effectively exterminate all possible life within a defined area. With traditional sterility indicators containing living spores, spore viability cannot be determined with any significant degree of precision. Conditions vary greatly during manufacture, transport, storage and use. Spore viability over these inconstant conditions is not accurately calculable. There are simply too many variables to consider and the requirements for variability, at least the few that are clearly definable, are as diverse as the genetic compositions of the spores themselves.

If bacterial spores can be thought of as networks of interacting enzyme systems surrounded by a cell wall, then when bacterial spores lose viability due to sterilization certain enzyme systems within the spore should also be inactivated. Consequently, it may be possible to use interactive enzyme systems instead of spores to determine whether sterilization conditions were met. These methods should comply with FDA standards for biological sterility indicators, would be highly efficient, easily standardized, and simple to use allowing those with even minimal training to achieve reliable results without the aide of specialized instruction, expense or instrumentation. There would also be no risk of microbial contamination associated with the test indicators themselves because no spores or other microorganisms would be introduced into the chamber despite the fact that the indicators provide the most biologically germane analysis available.

The invention provides processes and apparatus for determining the efficacy of a sterilization cycle based upon the recovery of activity of multiple, interacting, microbiologically-derived enzyme systems. Using the processes of the invention, sterility verification is determined from completion of the test results which, surprisingly, can be very rapidly achieved because the reliability of conventional biological indicators is combined with the speed of techniques closer to that utilized by enzymatic and chemical indicators. Further, and unlike spores, enzyme systems containing enzymes, coenzymes, catalysts, substrates or other reagents of an interactive system, viability is determined as stability and stability can be very precisely quantitated individually as well as in multiple enzyme systems. Therefore, using interactive enzyme systems not only is speed increased, but a level of standarization can be achieved which is far superior to that obtained with conventional biological or other enzymatic techniques.

The invention provides verification of the sterilization process in less than 60 minutes, preferably in about 5–15 minutes and more preferably in less than about 1 minute. This greatly increases the overall efficiency and safety of the operation of health care facilities by verifying sterility before utilization of the articles processed. The invention involves the rapid detection of any surviving interactive enzymatic activity which directly relates to the statistical probability of any surviving biological spores or other microorganisms in a test sample. Interactive enzyme systems comprise groups or collections of enzymes including coenzymes, cofactors, catalysts, substrates, and any other necessary reagents. Group interactivity is fundamentally distinct from any single or combination of single activities because, surprisingly, it provides a much more accurate reflection of the biological process without a need for living microorganisms. Further, it allows for increased flexibility with regard to different sterilization techniques, provides for sterility assurance unavailable with conventional techniques, and provides a wider range of sterility assurance for different microorganisms. For example, certain heat-stable organic molecules that are found loosely associated with an enzyme are often required for that enzyme reaction to proceed and are required for the functioning of other enzymes in the group. Inactivation of these molecules, which would not necessarily correlate with inactivity of an isolated enzyme, does correlate with sterility.

In one embodiment of the invention, the process comprises subjecting to a sterilization procedure at least one and preferably multiple components of an enzyme system. The enzyme system comprises a known mix of enzymes, coenzymes, catalysts, cofactors, substrates, other reaction reagents or combinations thereof, which is housed in a test indicator, preferably in a non-aqueous or only partially aqueous medium. The components have an interdependent activity which correlates with the viability of the microorganisms used in state-of-the-art biological indicators. Upon completion of the sterilizing process the test indicator, if necessary, is removed from the sterilization chamber and reacted with a specific mix of indicator reagents, the remaining components of the system. A positive result is only observed when each exposed component survives denaturization and is able to function interactively to produce a detectable enzyme-modified product. The enzyme-modified product as an indicator of residual activity is visually detectable within 1 to 60 minutes. Any change detected, which is preferably a color change, is an indication to an observer that the sterilization cycle had not inactivated certain components and thus, was insufficient to assure sterilization of other articles during the sterilization procedure. Conversely, an absence of a color change indicates that the sterilization procedure had inactivated at least one of the components thereby preventing the interactive reaction from taking place and thus, an equivalent of rapidly and directly detecting the survivability of bacterial spores in a similar conventional test. In other words, the lack of detectable enzyme-modified product within the established period of time indicates a sterilization cycle which has been lethal to the function of the interactive enzyme system as well as lethal to a viable $10^6$ population of *Bacillus stearothermophilus* spores. Generally, these values are expressed as D-values, which is the time taken at a given temperature to reduce the viable population of test microorganisms to ten percent of its original value.

The sterilization procedure useful in the practice of the invention may be, for example, a steam-pressure procedure or autoclaving, a chemical procedure utilizing ethylene oxide or another appropriately lethal chemical, dry heat of temperatures between about 50° C. to about 200° C., and radiation including gamma, beta and other forms of radiation. These procedures are practiced in the health care industry, but also in industries having to do with environmental technology, food manufacturing, waste disposal and in those technologies where absolute or near absolute sterility is required.

The test indicator, containing at least one and preferably a collection of components of a defined enzyme system on a solid support or in solution, is placed into a sterilization chamber. The sterilization procedure is performed within the chamber and, if necessary, the indicator is removed from the chamber and the remaining components of the system added to the indicator to form a mixture. The mixture is then incubated for a period of time sufficient to allow for product formation from the interaction of the enzymes with the substrate. Using radioactivity, enzymatic, electric or fluorometric activity, or in some other way, detectably labeled substrate, the product is detected using conventional techniques to determine the effectiveness of the sterilization procedure. According to this process, the biological interaction will occur only if the component(s) subjected to the sterilization process have not been destroyed or in some way inactivated. The relationship between the components is very relevant to a determination of sterility because it is not simply a chemical or enzyme reaction, but an enzyme interaction reflective of the presumptive physiological state of microorganisms within the chamber.

The ability of the methods of the invention to rapidly determine the efficacy of a sterilization cycle is based upon the discovery that the survival of functional capability of an enzyme system is necessary for the production of an enzyme-modified product. The rapidity of formation of the enzyme-modified product from the interacting enzymes is due, at least in part, to coimmobilization wherein the close proximity of two or more components of the enzyme system on a common solid support such that diffusion controlled exchange with bulk solution is limited. This process is further supplemented by component channeling or, the bringing together of two or more components of sequential reactions at a surface or microenvironment to further limit diffusion-controlled exchange with bulk solution. Component channeling with regard to enzymes is described in I. Gibbons et at. (Meth. Enzymol. 136:93–103, 1987) which is hereby specifically incorporated by reference.

The ability of the components of an enzyme system to survive conditions which only partially kill test microorganisms is dependent upon the use of a semipermeable, hydrophobic barrier between the sterilant and the enzymes, and that the interactive enzyme system will remain active following a sterilization cycle which is insufficient to kill the test microorganisms. This provides a direct correlation of spore viability with the interactive activity of the enzymes of the system which, following an inadequate sterilization cycle, is sufficient to convert a substrate system for those enzymes to a visually detectable concentration of product within a relatively short time, preferably 1 to 60 minutes. The basis for the correlation between the activity of the enzymes and other components to the germination and growth of microorganisms is due to the commonality of both in their reliance upon systems of biologically derived interacting enzymes and coenzymes to function. Typically, the survival of enzymes prior to sterilization is optimal in a nonaqueous environment. The nonaqueous medium enhances stability as well as creating a semi-permeable, time dependent barrier to the sterilant.

The sterility indicator demonstrates that there is a direct correlation between the conditions to kill a microorganism and the conditions to inactivate a component of a network of interacting enzymes. In the case of an amplification interactive enzyme system, if any one of the key enzymes, coenzymes, cofactors, substrates, catalysts, or other reagent components of the system are totally inactivated when an indicator solution is added, no color change will occur.

The enzymes useful in the practice of the present invention are enzymes including extracellular and intracellular microbiological enzymes, whose interdependent activities correlate with the germination and growth of microorganisms typically used in current state-of-the-art biological sterility indicators henceforth referred to as test microorganisms. By correlates it is meant that enzymatic interaction can be used to predict future growth of residual viable microorganisms remaining subsequent to partial, inadequate or unsuccessful sterilization. The components are ones that, following an inadequate sterilization cycle which is sublethal to the test microorganisms, remain sufficiently active to react with the remaining components of an enzyme system to produce a detectable enzyme-modified product within 1 to 60 minutes, yet be inactivated following exposure to sterilant that would be lethal to the test microorganisms. Preferably this product would be visually detectable. Examples of interactive enzymes include nearly any combination of, generally, a synthase and a catabolase such as transferases and epimerases; phosphatases and kinases or phosphorylases; dehydrogenases and hydrogenases or diaphorases; oxidases and deoxidases; esterases or diesterases and polymerases; phosphatases, dehydrogenases and diaphorases; dehydrogenases and reductases; and dehydrogenase and oxidoreductases. These enzymes catalyze the interconversion of one or more substrates and usually in association with a coenzyme or cofactor.

Examples of coenzymes and cofactors useful in the invention include nicotinamide adenine dinucleotide (NAD), NADH, NADP, NADPH, acetyl, biotin, coenzyme-A (CoA), components of the complement system, thiamine pyrophosphate (TPP), pyridoxal phosphate, cobamide, tetrahydrofolate, ravin and heine. These coenzymes catalyze the transfer of acyl groups (CoA), the transfer of groups derived from a ketone (TPP), the transfer of $CO_2$ (biotin), transamination, decarboxylation and raceimization of amino acids (pyridoxyl phosphate), carbon group transfers and reductions (tetrahydrofolate), and methly group transfers (cobamide). Redox reactions also play an important role in biological metabolism and their associated cofactors include, in decreasing order of potential, ferredoxin, lipoic acid, NAD and NADP, flavins and hemes. Flavins in flavoproteins and hemes in cytochromes are tightly bound to proteins and function more as prosthetic groups rather than as strictly defined cofactors. Additional catalysts may also be required components of an enzyme system. Examples of typical catalysts include metal anions or cations, other single elements, or certain complex substances such as a polysaccharide polymer, a lipid or other fatty acid, a membrane or an inert substance. Components which are substrates include, for example, saccharides or polysaccharides, nucleic acids or nucleotides, chemicals and chemical compounds, fatty acids, amino acids or peptides, and other more specialized substrates such as diphenyl tetrazolium bromide, phenyltetra-zolium violet, and ditetrazolium chloride which are visually detectable. Components may be detected using labeled substrates which are converted into identifiably products using labels such as a chromogenic substance, a fluorescent substance, a luminescent substance, a spatial chemical, a metallic substance, a stable isotope or a radioactive isotope. Each of these components whether they be enzymes, coenzymes, catalysts or substrates of an enzyme system can be subjected to a sterilization procedure as described herein to verify sterility in a more biologically relevant process than is presently currently available.

Another embodiment of the invention is directed to a biological process for determining the effectiveness of a sterilization procedure as described above wherein the components of an interactive enzyme system comprise an interactive cycle such as a fructose cycle (wherein fructose 6-phosphate is interconverted to fructose 1,6-diphosphate through the action of kinases and phosphatases), glycolysis including the kinase/phosphatase cycles, the galactosidase cycle (wherein galactose 1-phosphate is interconverted to glucose 1-phosphate through the action of uridyltransferases and epimerases), a substrate or futile cycle (an enzymatic cycle which accomplishes virtually nothing but the cleavage of a nucleotide triphosphate (NTP) to a nucleotide diphosphate (NDP) such as ATP to ADP or GTP to GDP through the action of kinases and phosphatases), the citric acid cycle or the tricarboxylic acid cycle (wherein pyruvate is interconverted to oxaloacetic acid in a multi-step process involving phosphatases, kinuses, epimerases, phosphorylases, and transferuses), cyclic phosphorylation, a malate/isocitrate cycle, a coupled oxidation-reduction cycle (wherein oxiduses and reductases add or remove certain electrons from a compound) such as the conversion of alpha-ketoglutarate to glummate and 6-phosphogluconate, or combinations thereof. These and other cycles are described in most biochemical textbooks such as *Biochemistry* 3rd Ed. (L. Stryer Ed., W. H. Freeman and Co., N.Y. 1988), and *Biochemistry* (D. E. Metzler Ed., Academic Press, N.Y. 1977), both of which are hereby specifically incorporated by reference.

According to this method, component(s) of an enzymatic biological cycle are subjected to the sterilization process. Inactivation of the component(s) inhibits completion of the cycle and the creation of any significant amount of product, thereby indicating that the sterilization process was successfully completed. The rapidity and sensitivity of detection of enzymatic activity is due to the formation of the enzyme-modified product from the network of interacting components of the enzyme system such as by enzyme cycling. Enzyme cycling is the interdependence of multiple enzymes on the interconversion of coenzymes between the enzymes such that the two enzymes create a conversion cycle of an intermediate having two forms. This network may comprise the continual interconversion of coenzymes between the interacting enzymes such as, for example, the interconversion of reduced acetyl enzyme A (Ac-CoA) to oxidized Ac-CoA. NAD or NADP to NADH or NADPH respectively, or NTP to NDP. Cycling may involve the substrate, an associated coenzyme, or the enzymes themselves, and it directly contributes to the rapidity by which results are obtained.

Figure 2:
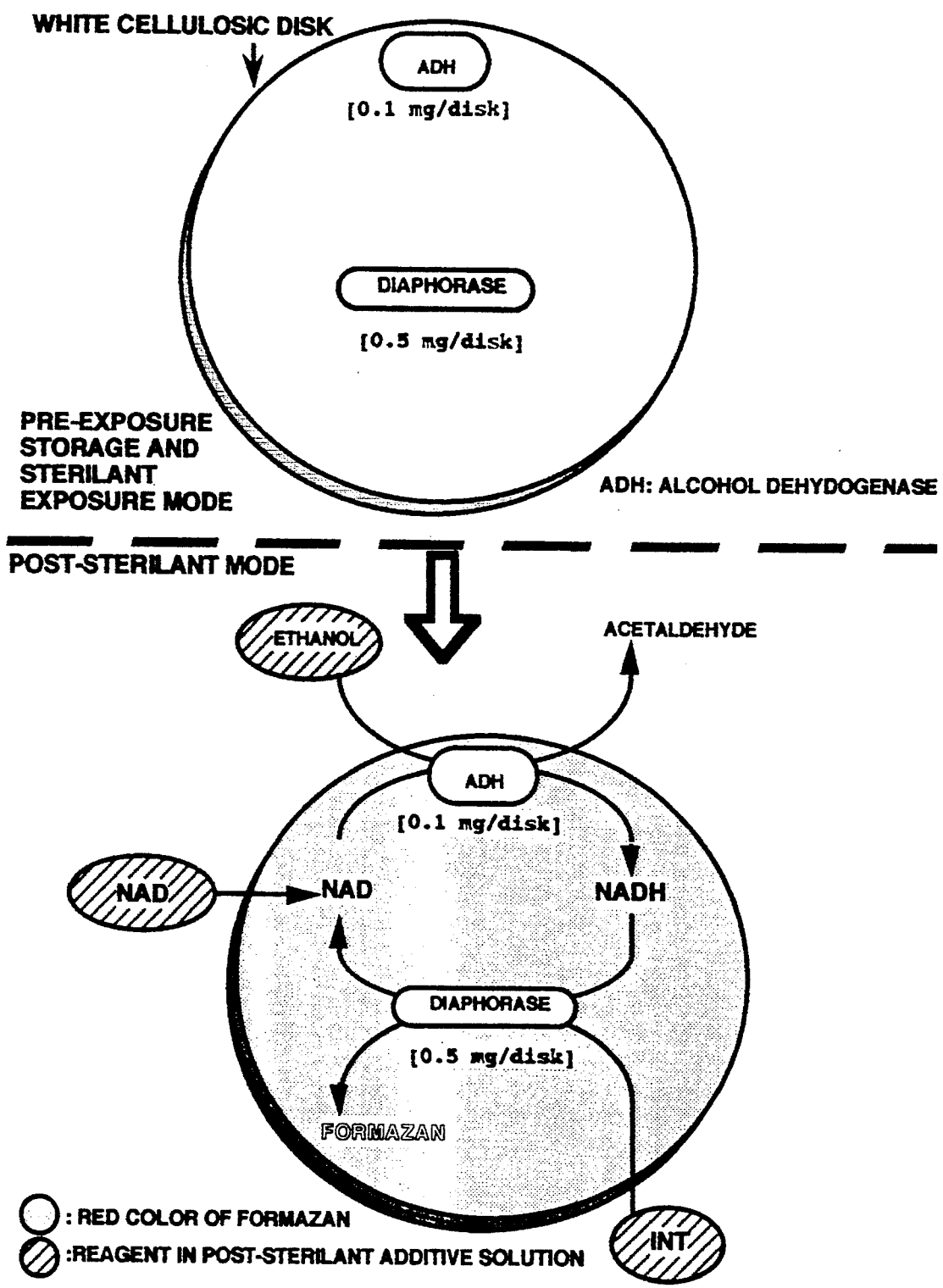
FIG. 2. Specific schematic of a two enzyme interaction of alcohol dehydrogenase/diaphorase and enzyme modified product, compound which is formed as a result of an enzyme catalyzed reaction, color development on a cellulosic disk.

For example, in FIG. 2, alkaline dehydrogenase and diaphorase are immobilized onto a cellulosic disk. The two enzymes create a conversion cycle of an intermediate having two forms—NA ⇔ NADH. Alcohol dehydrogenase catalyzes the conversion of ethanol to acetaldehyde with the help of a coenzyme, nicotinamide adenine dinucleotide (NAD), which is also converted into NADH. Diaphorase converts iodonitrotetrazolium (INT) to formazan while also re-converting NADH back to NAD. These two enzymes are coimmobilized on a solid support which is subjected to a sterilization cycle after which, NAD, ethanol and INT are added to form the complete enzyme system. The survival and successful interaction of all interactive enzymes of the test indicator for the production of visually detectable enzyme-modified product. In this case, acetaldehyde and formazan, a reduced form of a tetrazolium dye absorbing strongly in the visible range, are formed and easily detected.

Another embodiment of the invention is directed to a process for determining the effectiveness of a sterilization procedure comprising the steps as described above wherein the enzyme system comprises an amplification system. Amplification systems increase the amount of product formed in a cascading fashion. Enzymes of an amplification system are also described in most biochemistry textbooks such as *Enzymes*, 3rd Ed. (M. Dixon and E. C. Webb Eds., Academic Press, N.Y. 1979), which is hereby specifically incorporated by reference. The enzymes may also be such that visual detection of the enzyme-modified product is dependent upon survival of all different enzymes. Some natural processes are controlled by enzyme amplification systems (D. L. Bates, Annales De Biologie Clinique 47:527–32, 1989). The fibrin coagulation cascade, the trypsin/trypsinogen cascade, the complement cascade, and the kinase/phosphatase cycles of glycolysis are examples of enzyme amplification.

In an enzyme amplification cycle the product of one step is then used as a catalyst for the next step. A two enzyme disk system comprising trypsin and chymotrypsin would be a typical example. Chymotrypsin is added to a solid support and subjected to a sterilization cycle. Trypsin plus substrate would be added to the chymotrypsin at the conclusion of the cycle which catalyzes the conversion of substrate to product and also the conversion of chymotrypsin to trypsin. Consequently, from a very little bit of trypsin, assuming that the chymotrypsin has not been inactivated, a great deal of trypsin converted product can be created in very short order. Conversely, trypsin, substrate or coenzyme could be subjected to the sterilization cycle and chymotrypsin added subsequently to provide an alternative method of detection by enzyme amplification.

Overall, in an interactive enzyme system, it is usually not necessary to inactivate more than one component present to prevent the reaction product from forming. Enzymes which have been found to meet the above described requirements are those depending upon the oxidation or reduction of the coenzymes NAD, NADH, NADP, and NADPH. The mandatory nature of interdependence through conversion between reduced and oxidized forms of these coenzymes dictates that the enzymes occurs in pairs for which the first enzyme requires the oxidation of the reduced form of the coenzyme and the second enzyme requires the reduction of the oxidized form of the coenzyme. Such systems of enzymes include but are not restricted to alcohol dehydrogenase and cytochrome reductase (EC 1.6.99.3), glummate dehydrogenase and NAD(P) oxidoreductase (EC 1.4.1.3), and glucose-6-phosphate dehydrogenase and NADP 1-oxidoreductase (EC 1.1.1.49).

An enzyme system may comprise either the oxidized or reduced form of one of the aforementioned coenzymes, a chromogenic substrate (enzyme substrate which is converted, as a result of an enzymatic reaction, into a visually detectable colored enzyme-modified product) which, once acted upon by one of the enzymes, is converted into a visually detectable enzyme-modified product, any other enzyme substrates necessary for maintaining the enzymatically coupled oxidation-reduction cycling, and a buffered solvent.

When, for example, all or parts of the substrate system are to be included in the indicator device during sterilization, the included parts are not spontaneously broken down or converted to a detectable product during sterilization. Visualization of NAD(P)-dependent reactions can be accomplished by providing a substrate hydrogen acceptor in the substrate system which, while allowing the reoxidation of NAD(P)H, converts to a reduced form characterized by a shift in observable color. The preferred chromogenie substrates are tetrazolium salts which are colorless or weakly colored and are converted into intensely colored formazans by enzymatic reduction. Some examples of these chromogenie substrates include 3-( 4',5'-dimethylthiazol-2-yl)-2,4-diphenyltetrazolium bromide, 2-(p-iodophenyl)-3-(p-nitrophenyl)- 5-phenyltetrazolium violet, 2,2',5,5'-tetra-(p-nitrophenyl)-3,3, (3-dimethoxy- 4-diphenylene) ditetrazolium chloride, and 2,2'-di-(p-nitrophenyl)-5,5'-diphenyl- 3,3'-(3,3'-dimethoxy-4,4'-diphenylene) ditetrazolium chloride.

The reliance upon coenzyme cycling, such as NAD-dependent enzyme cycling, is a feature of one embodiment of the invention. Linking enzyme detection to repeating redox cycles enables a several order of magnitude increase in sensitivity to surviving enzyme (C. Self, J. Immunol. Methods 76:389–93, 1985). In the current invention enzyme cycling is a particular form of signal amplification which reduces the time needed for a visual color development by several orders of magnitude. Thus, the inclusion of NAD-dependent, multi-enzyme interactive system comprises a novel use for the determination of sterility which significantly improves the utility and rapidity over current state-of-the-art practices.

The concentration of the enzymes and enzyme substrates are dependent upon the identity of the particular substrate, the enzyme system, the amount of enzyme-modified product that is generated to be visually detectable, and the amount of time that one is willing to wait to determine whether active enzymes are present in the reaction mixture. The amount of time needed to generate visually detectable color is also a function of the spatial proximity of the interacting enzymes to one another. The placement of enzymes catalyzing sequential, cyclic reactions at a surface or microenvironment where diffusion-controlled exchange with the surrounding bulk solution is limited, such as by enzyme channeling, improves the rapidity of the reactions and decreases the time needed for the generation of visually detectable color.

This concept is illustrated for a general case in FIG. 1 for the case of two interacting enzymes, disk enzyme 1 and disk enzyme 2. The two enzymes are coimmobilized upon cellulose fibers in this example within close proximity, thus exhibiting enzyme channeling of the sequential reactions producing product 1C and product 2C. Since product 2C is needed for the re-production of product 1C by disk enzyme 1 this example is also an illustration of enzyme cycling. Note that disk enzyme 1 also converts substrate 1A into product 1B. In the case that disk enzyme 1 requires product 2C to carry out the enzymatic conversion of substrate 1A into product 1B, product 2C may be considered a coenzyme. Likewise, for the case of disk enzyme 2 requiring product 1C to carry out the conversion of substrate 2A into product 2B, product 1C may be considered a coenzyme for disk enzyme 2. This example also illustrates the use of a chromogenie substrate, substrate 2A, which disk enzyme 2 converts into visually detectable colored product 2B.

In FIG. 2, alcohol dehydrogenase and diaphorase are coimmobilized on a white cellulosic disk during sterilant exposure. In the subsequent post-sterilant mode the enzyme substrates ethanol and INT (p-iodonitrotetrazolium violet; 2-[4-4 iodophenyl]-3-[4-nitrophenyl]-5-phenyltetrazolium chloride) and the coenzyme NAD are added in the bulk indicator solution. The NAD is a coenzyme for the conversion by alcohol dehydrogenase of ethanol to acetaldehyde. In the process of the alcohol dehydrogenase catalyzed reaction, NAD is converted to NADH which, in time, is a coenzyme for the enzymatic conversion by diaphorase of INT to the visually detectable colored product, formazan. A second example (FIG. 3) represents three enzymes, alkaline phosphatase, alcohol dehydrogenase, and diaphorase coimmobilized upon a white cellulosic disk during sterilant exposure. In the subsequent post-sterilant mode the enzyme substrates, NADP, ethanol, and INT are added in the bulk indicator solution. Any surviving alkaline phosphatase will convert the substrate NADP into product NAD which then serves as a coenzyme for the above described enzyme cycling reactions, turning the white carrier red.

Figure 3:
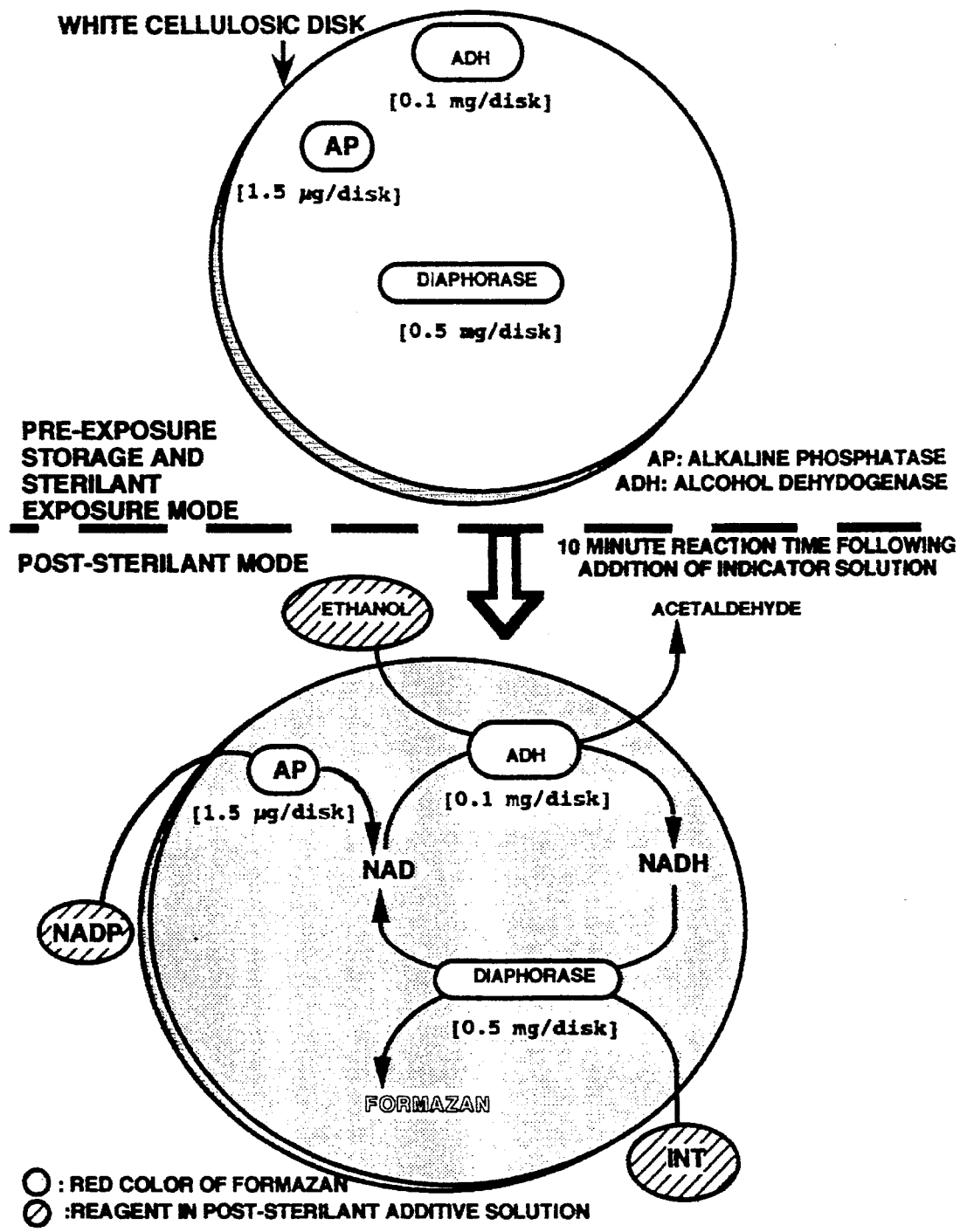
FIG. 3. Specific schematic of a three enzyme interaction of alkaline phosphatase/alcohol dehydrogenase/diaphorase and color development on a cellulosic disk.
Figure 4:
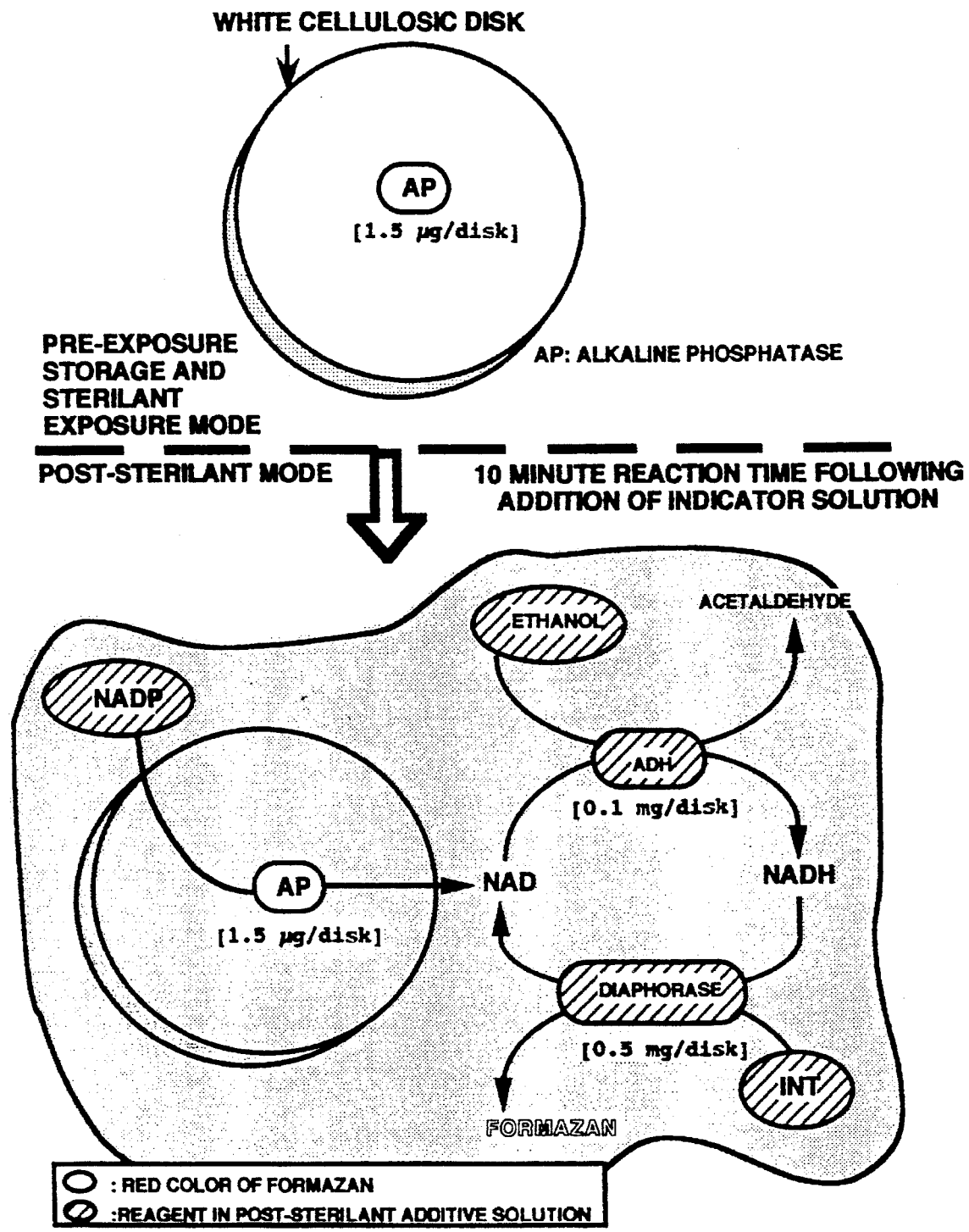
FIG. 4. Specific schematic of a single enzyme (alkaline phosphatase) on disk model with additional post sterilant enzyme interaction (alcohol dehydrogenase) for amplification and color development on a cellulosic disk.
Figure 5:
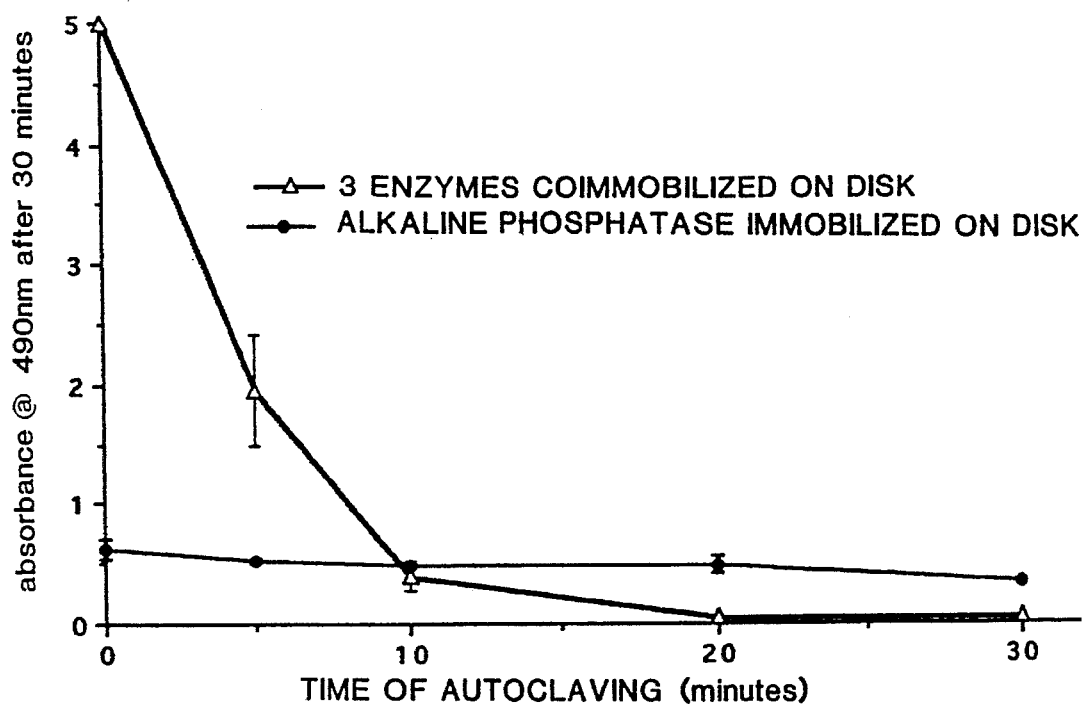
FIG. 5. Comparison of thermostability and extent of reaction of single component (enzyme) immobilized verses multiple components (enzymes) immobilized on disks.

The multiple interacting enzymes or other components may be physically separated as illustrated in FIG. 4. In this depiction, only the alkaline phosphatase is immobilized upon a white cellulosic disk during sterilant exposure. In the subsequent post-sterilant mode, multiple interacting enzymes in the form of diaphorase and alcohol dehydrogenase are added along with required coenzymes and enzyme substrates into the bulk indicator solution. The enzymatic conversions in this embodiment are the same as those wherein all three enzymes are coimmobilized except that only the survival of one enzyme, alkaline phosphatase, is subjected to survival stress in the form of sterilant exposure. In each of the above examples, the survival of activity of all enzymes is required in order for the generation of the visually colored enzyme-modified product, formazan. As shown in FIG. 3, coimmobilizing three enzymes results in dramatic increase of rapidity of formation of the formazan when compared with immobilization of the single enzyme (FIG. 4). This result is represented graphically in FIG. 5 wherein the thermostability of alkaline phosphatase verses the thermostability of three enzymes, coimmobilized on a disk, are compared. As shown, the presumed activity, as measured by absorbance, of the three enzyme system rapidly and dramatically decreased. The single enzyme started with little activity and decreased slowly.

An alternative embodiment of the invention is directed to a process as described above wherein an inhibitor of an enzyme system is subjected to inactivation in a sterilization procedure and the components of the enzyme system are subsequently added to assay the state of the inhibitor. If the inhibitor survived or was not otherwise destroyed by the sterilization procedure, the enzyme system will not function. Examples of such inhibitors include α-amino-oxyacetic acid which is a general inhibitor of pyridoxal phosphate-dependent enzymes (amino acid transaminases and decarboxylases), antabuse which inhibits oxidation of acetaldehyde by inhibiting alcohol dehydrogenase, flavianic acid which inhibits glutaminase, sodium iodoacetic acid and pyrazole which inhibit certain dehydrogenases including alcohol dehydrogenases, isopropyl hydrazine which inhibits diamine oxidases, parapyruvate which inhibits many oxidation reactions, oxamic acid which inhibits lactic dehydrogenase, phenylmethane sulphonyl fluoride and chymostatin which are specific inhibitors of trypsin and chymotrypsin, tartaric acid which inhibits phosphatases, and other inhibitors such as tosyl-lysine chloromethylketone (TLCK) and tosyl-phenylalanine chloromethylketone (TPCK).

Another embodiment of the invention is directed to a test indicator for determining the effectiveness of a sterilization procedure. In its simplest form, a sterility indicator useful in practicing the method of the invention includes a source of multiple interacting enzymes in a container having a liquid impermeable and substantially gas non-adsorptive wall, at least one opening covered with a gas-transmissive cover, said opening leading into a chamber which contains one or more components of the interactive enzyme system with a liquid impermeable barrier between the components and the opening. The interacting components are localized within close proximity to one another such as within the matrix of a cellulose filter disk and/or within a defined medium and are thus, coimmobilized. One or more enzymes, substrates, coenzymes or catalysts may be included on the solid matrix. Within the container is an effective amount of a material to form the barrier which is semi-permeable, but not freely or wholly permeable to the transmission of liquids and gasses, and an effective means for maintaining a finite distance between the semipermeable opening and the enzymes. The barrier may be liquid permeable or impermeable and may be a plunger or stopper, but is preferably a sponge which reduces the likelihood of slippage that may sometimes occur with plungers and stoppers. Also preferable is a barrier which is a membrane that is constructed of a polymer such as a synthetic, a plastic, a rubber, Gortex (a gas transmissive and liquid impermeable polymer) or a combination thereof. A Cortex membrane would be liquid impermeable whereas a sponge barrier would be liquid semi-permeable.

The defined medium may be hydrophilic, but is preferably hydrophobic, for example non-aqueous, yet may be semi-permeable or transmissive to gases including steam sterilant. The medium may be non-aqueous as may be the immediate environment surrounding the components during storage prior to exposure to sterilizing conditions. The operational stability of a component is generally reliant upon maintenance of a non-aqueous enzyme environment of the medium. The theoretical basis for this requirement is well-developed (A. Zaks et at., J. Biol. Chem. 263:3194–3201, 1987). The degree to which the component is susceptible to damage by the sterilization process correlates directly with the degree to which moisture in the form of steam is allowed to interact with the enzyme source during the course of steam processing (A. M. Klibanov, Advances in Applied Microbiology 29:1–28, 1983). The components may be immobilized on a solid support such as a support comprising cellulose, plastics, glass, ceramics, membranes, polymers, or combinations thereof. Preferably, the solid support is a highly compartmented cellulosic disk suspended in an anhydrous medium.

The current invention is unique due to the speed at which a result can be obtained and also certain preferred embodiments which are based on non-aqueous systems. The test indicator preferably utilizes mineral oil as the nonaqueous medium which has many functions within the system. Mineral oil comprises a mixture of liquid hydrocarbons obtained from petroleum having specific gravity between 0.818 and 0.880, a kinematic viscosity of not more than 33.5 centistokes at 40° C., and that meets the requirements for neutrality, readily carbonizable substances, limit of polynuclear compounds and solid paraffin set by USP XXII. The oil is used to cover the solid support disk upon which multiple interacting enzymes are coimmobilized, providing a non-aqueous environment to stabilize the enzymes. The oil creates a barrier to water and air which could have detrimental effects on the enzymes while in storage. The oil also acts as a semi-permeable barrier to steam when the rapid enzymatic indicator is exposed to a steam sterilization cycle. By varying the amount of oil, or the anhydrous nature of the immediate environment, the amount of steam reaching the disks with the enzymes can be precisely controlled.

An alternative embodiment of the invention is directed to a two-stage biological indicator for determining the effectiveness of a sterilization procedure comprising a test indicator containing two vials. In the first is a network of interactive components of an enzyme system such as described above. In the second vial is a culture of microorganisms. A two stage test indicator of the invention provides a double indication of the effectiveness of the sterilization procedure. Basically, substrate is added to the enzymes and immediately analyzed by the process herein described to get a first stage indication. The remaining spores of the second vial are incubated under culturing conditions for a longer period of time to provide a second stage indication of sterility. Useful microorganisms of the two-stage indicator include spore populations of the genus Bacillus, Neurospora, Candida, and Clostridium. The first incubation period is very rapid as described above, and may be less than 60 minutes, preferably less than 15 minutes and more preferably less than one minute. The second incubation period may be between about 2448 hours, preferably about 1 to 24 hours, more preferably less than about 6 hours and even more preferably less than about one hour.

Another alternative embodiment of the invention is a self-contained test indicator for determining the effectiveness of a sterilization procedure comprising an outer container having liquid impermeable and substantially gas non-absorptive walls and at least one opening covered with a gas-transmissive cover, said opening leading into a chamber that contains a first and a second vial wherein the first vial has at least one opening that is covered with a gas-transmissive cover and contains interactive components of an enzyme system, and the second vial contains any remaining components which, when mixed with the components of the first vial, produces a detectable product, said vials being constructed of a material which can be opened and their contents mixed without being removed from the test indicator. An example of such a construction is an ampule having heat stable walls with inner chambers. The chambers include one pair of chambers, which are separated by a collapsible or otherwise crushable divider, which together contain all of the components of an interactive enzyme system as described herein. The ampule also contains another pair of chambers, separated by a collapsible or crushable divider, one of which contains a spore sample and the other a sample of media for incubating the spores.

The amount of components are such that any enzyme activity remaining after an inadequate sterilization cycle is detectable. The components including enzymes, coenzymes, cofactors, catalysts, substrates and any other necessary reagents are incubated and determined after they are subjected to the sterilization cycle. Incubation is continued over a period of time and under conditions sufficient to liberate a detectable amount of enzyme-modified product, assuming that any of the enzymes remain active. In general, the incubation time required is between 1 minute and 60 minutes and the incubation temperature is between about 20° C. to about 70° C.

Generally, commercial methods for detecting enzyme-modified product utilize advanced instrumentation such as fluorimeters and spectrophotometers. For the purpose of this invention, a visual detection method for the measurement of enzyme-modified product is preferred due to simplicity of method and rapidity of results. For example, the specific enzyme substrate may comprise a tetrazolium salt which, on interaction with an NADH-dependent oxidoreductase enzyme gives rise to a colored formazan which is visually detectable. The process of the invention permits very rapid determination of enzyme activity which can be used to predict conditions permitting survival of microorganisms and thus, sterilization efficacy. The enzyme determination test used utilizes only a short period of incubation, usually from about 1 to 60 minutes, to provide sufficient enzyme-modified product for visual detection.

Figure 6:
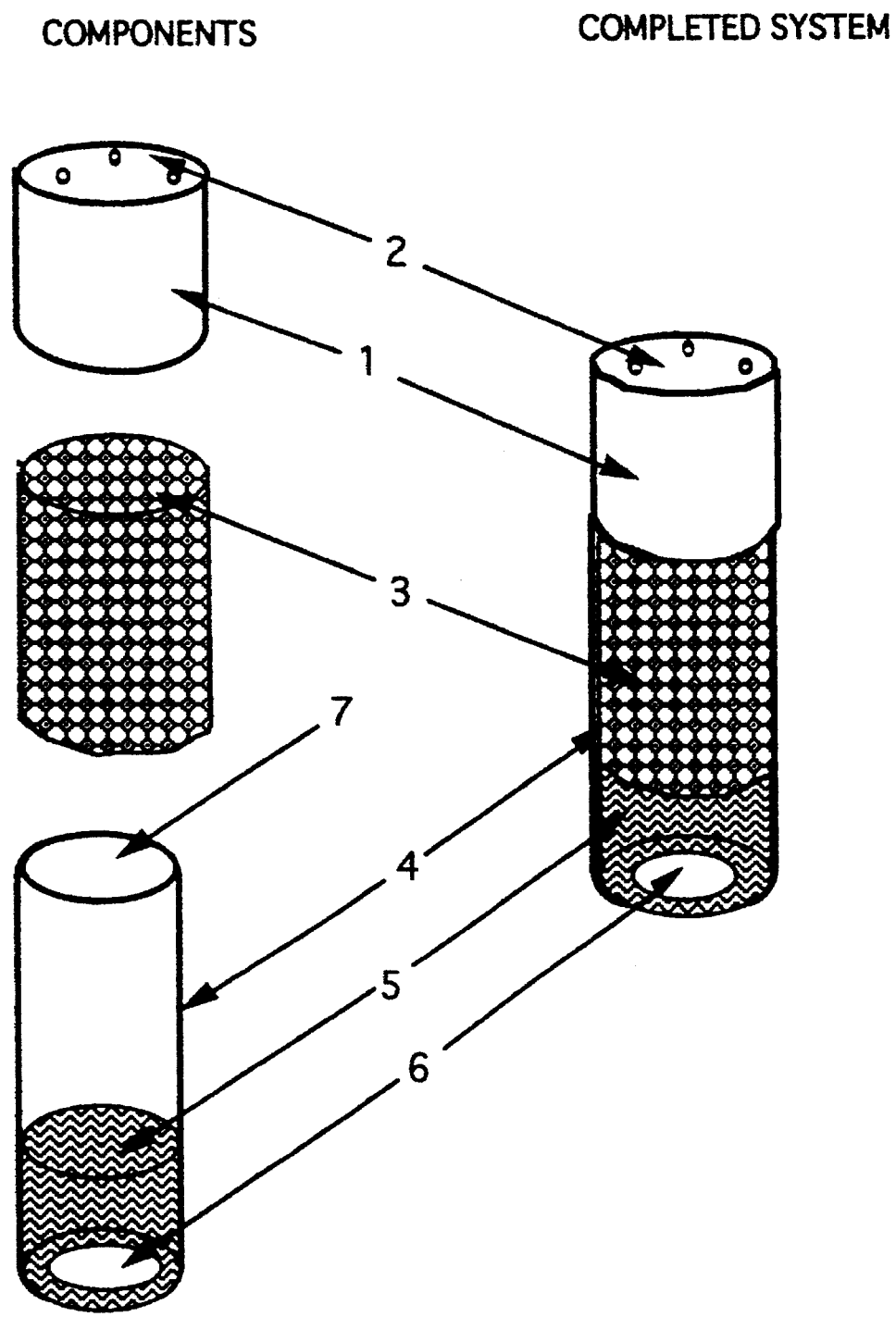
FIG. 6. Diagram of container construction.

A rapid multiple enzyme sterility indicator of the invention is illustrated in FIG. 6. The container is a cylindrical tube 4 having liquid impermeable walls with an opening 7 at one end. Tube 4 contains a solid support disk 6 upon which multiple interacting enzymes are coimmobilized. Tube 4 also contains a non-aqueous medium 5 covering solid support disk 6. Opening 7 is covered with a cap 1 having holes 2 allowing unimpeded access of sterilant through opening 7. The apparatus of FIG. 6 is assembled by placing solid support disk 6, upon which multiple interacting enzymes are coimmobilized, into the bottom of tube 4. Non-aqueous medium 5 is added to cover solid support disk 6. A cylinder of heat resistant foam material 3 is compressed into tube 4 providing a structural framework for the containment of nonaqueous medium 5. Foam material 3 also serves to maintain a fixed distance between the multiple interacting enzymes coimmobilized upon solid support disk 6 and opening 7. Cap 1 is placed on top of tube 4 covering opening 7.

Figure 7:
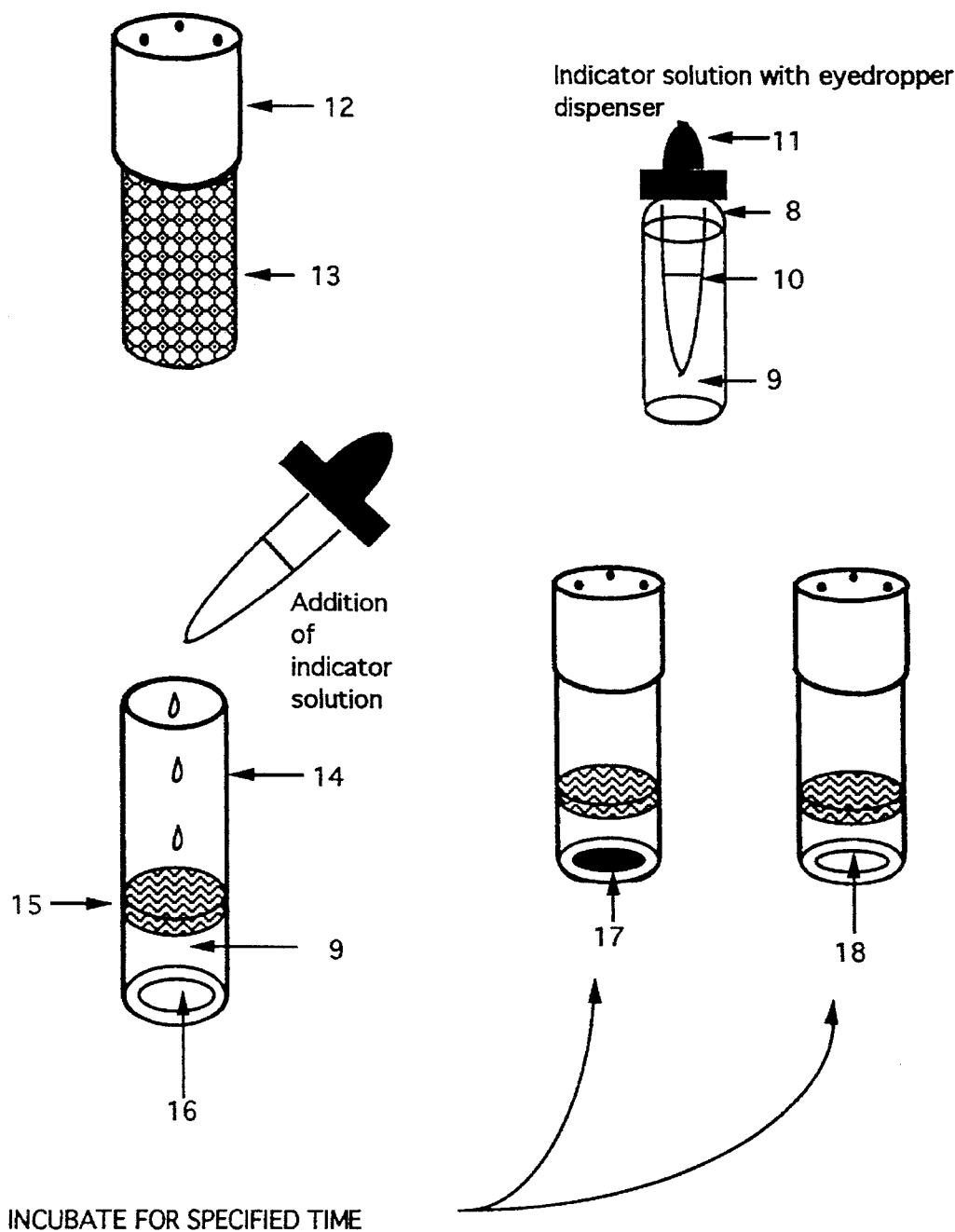
FIG. 7. Diagram of preferred operation of multiple component container.

The dispenser of the indicator solution is shown in FIG. 7. The bottle 8 contains the indicator solution 9 which produces a visual color change when exposed to active multiple interacting enzymes coimmobilized on solid support disk 16. The bottle 8 contains an eyedropper 11 with a premeasured volume line 10. Filling the eyedropper 11 to the premeasured volume line 10 with indicator solution 9 assures that the correct volume of indicator solution 9 is dispensed into tube 4.

A method for conducting the sterility test is illustrated in FIG. 7. The sterility indicator is placed into the sterilizer along with other materials which are to be sterilized. The sterility indicator is exposed to the sterilant during the course of a sterilization cycle. After the completion of the sterilization cycle, the sterility indicator is removed from the sterilizer and allowed to cool to room temperature. The cap 12 and the foam material 13 are removed. The indicator solution 9 is drawn into the eyedropper 11 using the premeasured volume line 10 to assure that the correct volume if indicator solution 9 is used. Indicator solution 9 is dispensed into tube 14. The incubator solution is incubated at room temperature with the enzymes coimmobilized on the solid support for 1 to 60 minutes, preferably for less than 10 minutes. The solid support disk is visually inspected at the end of the incubation period. The absence of red coloration on the solid support disk indicates negative result 18 and signifies a successful sterilization cycle. The presence of red coloration on the solid support disk indicates positive result 17 and signifies an unsuccessful sterilization cycle.

The following examples illustrate embodiments of the invention, but should not be viewed as limiting the scope of the invention.

EXAMPLES

Example 1

The two enzyme system is composed of alcohol dehydrogenase (445 U/mg P, Worthington Biochemical) and diaphorase (30.8 U/mg DW, Worthington Biochemical). The alcohol dehydrogenase was used at a preferred concentration of 5.0 mg/ml and within a range of 0.5 mg/ml to 250 mg/ml. The diaphorase was used at a preferred concentration of 25 mg/ml, but may be used within a range of about 2.5 mg/ml to 1.25 g/ml. The enzymes are dissolved in an aqueous buffer such as phosphate buffered saline (PBS) or 0.05M Tris buffer, pH 8.5 and dialyzed. Spectrapor molecular porous membrane tubing, molecular weight cut-off of 3500 daltons, was used for dialysis of all enzymes. The tubing was boiled in 2% sodium bicarbonate, 1 mM EDTA for 10 minutes, rinsed in running tap water for one hour and finally rinsed ten times in distilled water and stored at 2°–8° C. in distilled water. Tubing was cut to size, tied at one end, filled with enzyme solution, and knotted at the other end. Dialysis was performed 100 times the volume of enzyme solution using 0.05M Tris buffer, pH 8.5, and twice dialyzed for four hours and once more for 14–18 hours at 2°–8° C. with gentle stirring. The 20 ul of the enzyme solution was transferred onto white cellulosic solid support disks by dispensing 20 ul onto each disk. The disks, housed in a multiwell microtiter plate, were immediately frozen to −71°. The disks were then freeze-dried by placing the frozen disks, in microtiter plate, into a lyophilization bottle and applying a vacuum of greater than 200 microns mercury for a minimum of three hours. The disks containing coimmobilized enzymes were stored in a non-aqueous environment within clear vials covered by mineral oil prior to use as a sterility indicator. The anhydrous medium or mineral oil was held in place within the clear vial by means of a material added to the vial which physically separates the anhydrous medium from the air space of the vial container. The separator was a heat resistant sponge material cut in a cylinder which was physically placed in the vial until its lower surface came in direct contact with the anhydrous medium which in this case was oil.

The indicator solution is a dear, colorless solution, but when added to multiple interacting enzymes, the enzymes react with the indicator solution to produce an enzyme-modified colored reaction product. The indicator solution contains p-Iodonitrotetrazolium violet (2-[4-Iodophenyl]-3-[4nitrophenyl]5-phenyltetrazolium chloride) within a range of $3.2 \times 10^{-5}$ M to $0.16 \times 10^4$M, preferably $3.2 \times 10^{-3}$M; NAD (B-nicotinamide adenine dinucleotide) within a range of 1 $1 \times 10^{-6}$M to $5.5 \times 10^{-3}$M, preferably $1.1 \times 10^{-4}$M; ethanol within a range of 1% to 100% (by volume), preferably 5.5%. The preferred buffer was 0.5M Tris, pH 8.5.

Example 2

This example illustrates the rapidity and simplicity of use of the current invention. In this example alcohol dehydrogenase and diaphorase were coimmobilized onto white cellulosic disks as previously described and illustrated in FIG. 2. The disks were placed in the test vial as described previously and illustrated in FIG. 6. The test vials were autoclaved in replicates of 4 for intervals of 5 and 15 minutes. The vials were removed from the autoclave and allowed to cool. The sterility indicator test was performed as previously described and illustrated in FIG. 7 using an indicator solution composed of Tris buffer, ethanol, NAD, and INT. After a ten minute incubation at room temperature, a visual recording of the vials containing the indicator solution and cellulosic disk upon which the two interactive enzymes were coimmobilized was made by placing the vials on a glass platform and viewing and/or videotaping the disks from below. The resulting video images were captured digitally using Adobe Photoshop software and the relative color intensity on the disks was quantified using the histogram function of the software. The vials were also visually, qualitatively-rated as either positive, red colored, or negative, having no visual sign of red color.

Figure 8:
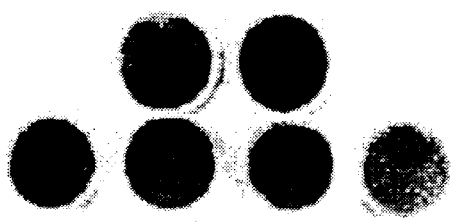
FIG. 8. Photograph of sample disks with computed color densities.
Figure 9:
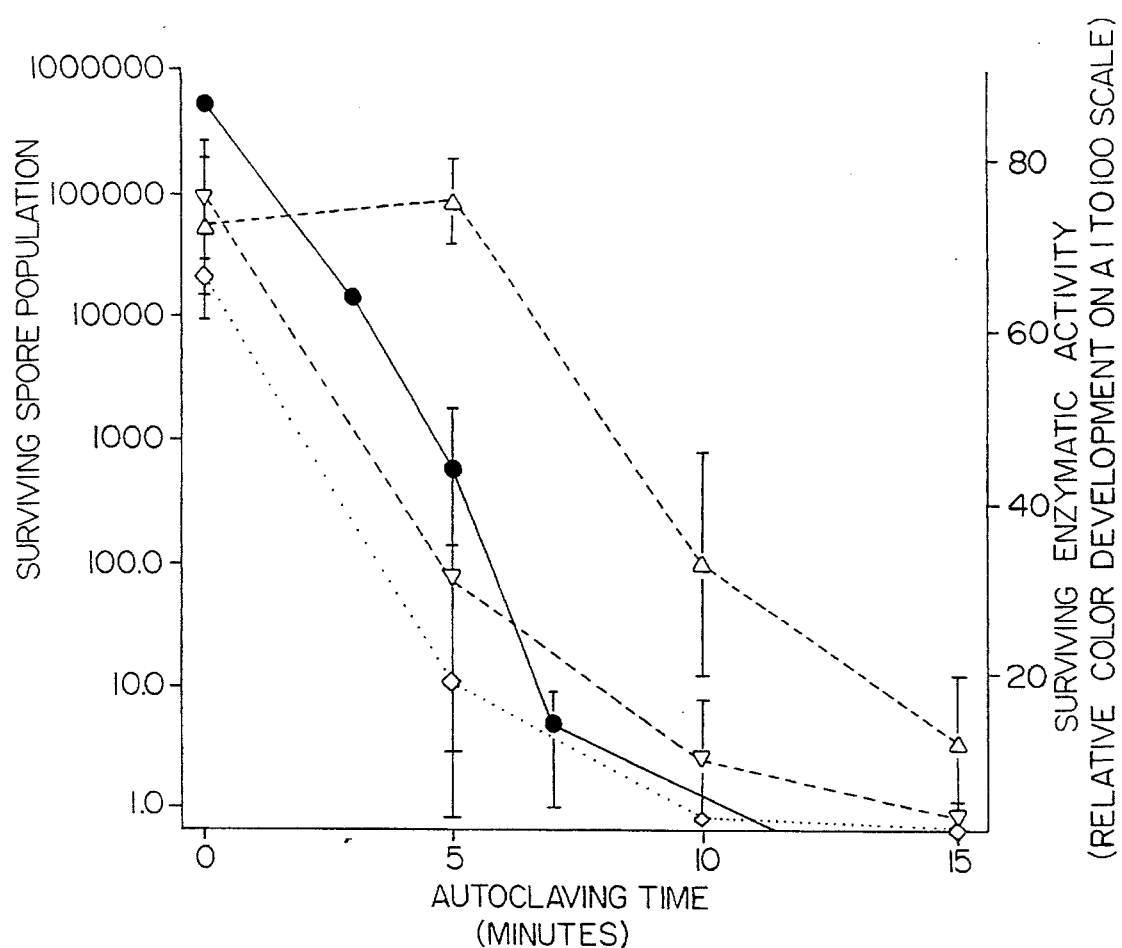
FIG. 9. Relationship of the multiple enzyme system to viable *Bacillus stearothermophilus* spore inactivation.
Figure 10:
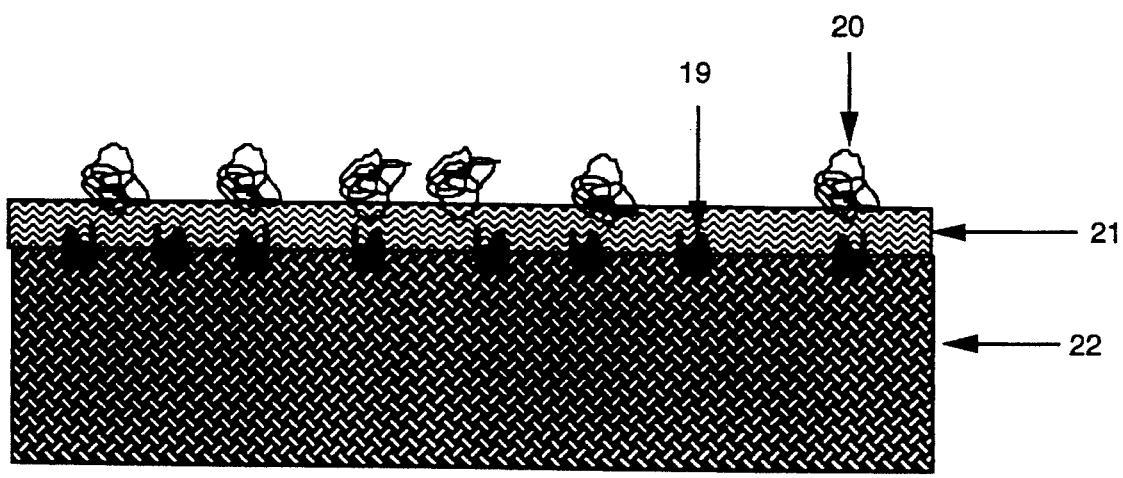
FIG. 10. Diagram of layered solid support.

The results of this example are presented in FIG. 8. After 5 minutes of autoclaving, all replicates of the rapid enzyme indicator demonstrated strong positive color production after a short ten minute incubation. Rapid Enzyme Sterility Indicators which were autoclaved for 15 minutes demonstrated no color either quantitatively or qualitatively by visual inspection. FIG. 9 illustrates a plot of the quantitative determination of color intensity of the Rapid Enzyme Sterility Indicator of the current invention versus time of sterilant exposure-in this example using steam autoclaving at 121° C. The activity of the enzyme system in various configurations of oil can be compared which serves to feature the influence of a hydrophobic environment. Overlaid on the same plot is data depicting the logarithm of number of surviving *Bacillus stearothermophilus* microorganisms isolated from Sportrol biological indicators versus steam autoclaving time. Sportrol is a non-self-contained biological indicator. The close correspondence of the plots supports the claim of the current invention that the enzymes useful in the practice of the present invention are extracellular and intracellular microbiological enzymes, whose interdependent activity correlates with the germination and growth of microorganisms typically used in current state-of-the-art biological sterility indicators.

Example 3

This example illustrates the correlation between a conventional biological sterility indicator containing spores and a rapid enzymatic indicator. The conventional biological sterility indicator used for the comparison was the commercially available Sportrol Spore Strip from North American Science Associates, Incorporated in Northwood, Ohio. It was compared to the rapid enzymatic indicator (two enzyme system) at 121° C. in a bier vessel (biological indicator-evaluator resistometer vessel used to deliver precisely controlled sterilizing conditions). Both sterility indicators were tested after 5, 7, 8, 9, 10, 11, 12, 13 and 15 minutes of exposure time in the bier vessel.

The Sportrol Spore Strip was placed in nutrient medium and incubated after it has been exposed to the bier vessel for its designated time. After one day, the tubes were checked and the number of tubes with viable spores. (growth) are recorded as positives. The tubes were incubated up to 7 days and any observed growth in the tubes was recorded as a positive.

The rapid enzymatic indicator has indicator solution, containing INT, ethanol, and NAD in buffer, added into the vial after it had been exposed to the bier vessel for its designated time. The rapid enzymatic indicator contains two enzymes, diaphorase and alcohol dehydrogenase, normally found in indicator microorganisms, coimmobilized on a white cellulose disk. After the addition of the colorless indicator solution to the disk, the vial was incubated at room temperature for between about 2 to about 30 minutes. After the incubation period, the disk was visually inspected for any signs of color. If any red color was seen on the disk, the result was recorded as a positive. A positive result indicates proper sterilization conditions were not met. Color developed on the disk because the enzymes were not totally inactivated. If the disk remains totally white, the result was recorded as a negative. A negative result shows proper sterilization conditions were met and the enzyme(s) were inactivated.

The number of positive results for the Sportrol biological indicator were determined after the 7 day incubation period. The number of positives for the rapid enzymatic indicator were determined 30 minutes after the indicator solution was added. The number of positives for each time point were similar for the two different types of indicators.

The outgrowth and viability of spores in the Sportrol indicator was similar to the enzymatic activity of the rapid enzymatic indicator. Hence the enzymatic indicator can produce a similar result as the Sportrol biological indicator. By correlating spore viability after sterilization to enzymatic activity of enzymes derived from microorganisms, it creates a rapid process to check the efficiency of sterilizers. Once the process to ensure proper sterilization conditions does not rely on the growth of microorganisms, the indicator test results were available after minutes instead of hours or days.

Example 4

Example 4 illustrates the applicability of the Rapid Enzyme Sterility Indicator of the present invention for use in flash sterilization. Flash sterilization produces a more rapid sterilization cycle at a temperature of 132° C. by increasing the chamber pressure. This increase reduces the time necessary to destroy viable test microorganisms from 15 minutes in the case of steam sterilization at 121° C. down to 2 minutes in the case of flash sterilization at 132° C. In this example, cellulose disks containing coimmobilized diaphorase and alcohol dehydrogenase as illustrated in FIG. 2 were placed in the indicator vial as described previously and illustrated in FIG. 6. Vials were autoclaved at 132° C. for two minutes and subsequently removed from the autoclave and allowed to cool. The sterility indicator test was performed as previously described and illustrated in FIG. 7 using an indicator solution composed of Tris buffer, ethanol, NAD, and INT. After a ten minute incubation at room temperature, results indicated that vials were qualitatively rated as negative having no visual sign of red color.

Example 5

Example 5 illustrates another embodiment of the invention which operates in a totally non-aqueous environment. Conducting the enzymatic reactions in a non-aqueous medium can enhance enzymatic reaction kinetics and improve recovery of enzymatic activity (A. Zaks et at., J. Biol. Chem. 263:3194–3201, 1988). In this example, alcohol dehydrogenase and diaphorase were coimmobilized with the coenzyme NAD onto white cellulosic disks. Disks were placed in the indicator vial as described previously and illustrated in FIG. 6. Vials were autoclaved 15 minutes, removed from the autoclave and allowed to cool. The sterility indicator test was performed as previously described and illustrated in FIG. 7 using an indicator solution composed of INT dissolved in 100% ethanol. After a one to twenty minute incubation at room temperature, a visual determination of color production within the vials containing the indicator solution and cellulosic disk upon which the two interactive enzymes were coimmobilized was made to determine whether sterilization was complete.

Example 6

In this example, a layered solid support construct was utilized. The construct begins with the solid support 22, then the alcohol dehydrogenase 19 was immobilized onto the disk and the enzyme and disk were frozen. After freezing the alcohol dehydrogenase was covered by a layer of gelatin solution 21 which forms a matrix using amphoterically-charged organic molecules over the alcohol dehydrogenase. Once the gelatin hardened, the diaphorase was added on top of the gelatin. The construct was then freeze-dried and the disks placed in the indicator vials as previously described in FIG. 6. Vials were autoclaved for 15 minutes, removed from the autoclave and allowed to cool. The sterility indicator test was performed as previously described and illustrated in FIG. 7. After incubation at room temperature, a visual determination of color production on the disks was made. This layered construct greatly increased the stability of the alcohol dehydrogenase under the gelatin layer while still allowing for optimal diffusion of chromogenic substrate from the bulk solution to the diaphorase layer outside of the gelatin.

Example 7

In this example, two enzymes were coimmobilized onto a solid support via site-to-site directed enzyme complexes (N. Siegbahn et at., Methods Enzymol. 136:103–113, 1987). In this configuration interconversion of coenzymes between the two enzymes proceeds at greatly enhanced rates. This enhancement produces a Rapid Enzyme Sterility Indicator having greater sensitivity and rate of visual color development. Using this disk structure, the Rapid Enzyme Sterility Indicator was constructed as illustrated in FIG. 6. After autoclaving for a specified time period the Rapid Enzyme Sterility Indicator was operated as described previously and illustrated in FIG. 7. The vials were visually inspected after an incubation of from one to twenty minutes. The presence or absence of color development indicated the partial or complete status of the sterilization cycle.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

We claim:

1. A biological process for determining the effectiveness of a sterilization procedure comprising the steps of:
   a) placing a test indicator containing one or more components, but not all of the components of a plurality of interactive enzyme systems into a sterilization chamber;
   b) performing the sterilization procedure within the chamber;
   c) adding the remaining components of the plurality of interactive enzyme systems to the one or more components in the test indicator to form a mixture;
   d) incubating the mixture for a period of time; and
   e) detecting presence or absence of a detectable product to determine the effectiveness of the sterilization procedure.

2. The process of claim 1 wherein the sterilization procedure is selected from the group consisting of steam-pressure procedures, chemical procedures, dry heat procedures, radiation procedures, and combinations thereof.

3. The process of claim 1 wherein the plurality of interactive enzyme systems comprise an enzyme cycle selected from the group consisting of a futile cycle, a glycolysis cycle, a galactosidase cycle, a phosphorylation cycle, a malate/isocitrate cycle, a citric acid cycle, a coupled oxidation-reduction cycle and a combination thereof.

4. The process of claim 1 wherein the plurality of interactive enzyme systems comprise an enzyme amplification cycle selected from the group consisting of a fibrin/coagulation cascade, a trypsin/trypsinogen cascade, a complement cascade and combinations thereof.

5. The process of claim 1 wherein the one or more components subjected to the sterilization procedure are coimmobilized on a solid support.

6. The process of claim 1 wherein the incubation period is less than about 1 hour.

7. The process of claim 1 wherein the incubation period is less than about 15 minutes.

8. The process of claim 1 wherein the plurality of interactive enzyme systems comprise components selected from the group consisting of enzymes, coenzymes, cofactors, prosthetic groups, catalysts and substrates.

9. The process of claim 8 wherein the enzymes are selected from the groups consisting of alkaline phosphatases, alcohol dehydrogenases and diaphorases; alcohol dehydrogenases and cytochrome reductases; glutamate dehydrogenases and oxidoreductases; and glucose- 6-phosphate dehydrogenases and nicotinamide adenine dinucleotide and nicotinamide adenine dinucleotide phosphate oxidoreductases.

10. The process of claim 8 wherein the coenzyme, cofactor or prosthetic group is selected from the group consisting of nicotinamide adenine dinucleotide reduced nicotinamide adenine dinucleotide, nicotinamide adenine dinucleotide phosphate, reduced nicotinamide adenine dinucleotide phosphate, acetyl-coenzyme A, thiamine pyrophosphate, components of the complement system, pyridoxal phosphate, biotin, tetrahydrofolate, cobamide, flavin and heme.

11. The process of claim 8 wherein the substrate is selected from the group consisting of chromogenic substances, fluorescent substances, luminescent substances, spatial chemicals, metallic substances, stable isotopes and radioactive isotopes.

12. The process of claim 11 wherein the chromogenic substance is a tetrazolium salt selected from the group consisting of diphenyl tetrazolium bromide, phenyltetrazolium violet, and ditetrazolium chloride.

13. A microorganism-free process for determining the microorganism survivability of a sterilizing environment comprising the steps of:
   a) exposing one or more components, but not all of the components of a plurality of interactive enzyme systems to a sterilizing environment;
   b) adding the remaining components of the plurality of interactive enzyme systems to the one or more components which were subjected to the sterilizing environment; and
   c) detecting activity of the plurality of interactive enzyme systems to determine the microorganism survivability of the sterilizing environment.

14. The process of claim 13 herein the one or more components subjected to the sterilizing environment are at least partially contained in an anhydrous carder.

15. The process of claim 13 wherein the one or more components subjected to the sterilizing environment are fixed to a solid support which is a cellulosic disk with multiple layers of amphoterically-charged organic molecules, each layer containing at least one component of the enzyme system.

16. The process of claim 13 wherein the one or more components of the plurality of interactive enzyme systems comprise at least two enzymes and the enzymes are contained on a solid support disk wherein each enzyme is physically positioned such that an active site of one enzyme is in direct opposition to an active site of an other enzyme.

17. A microorganism-free process for determining the microorganism survivability of a sterilizing environment comprising the steps of:
   a) exposing an inhibitor of a plurality of interactive enzyme systems to a sterilizing environment;
   b) adding the remaining components of the plurality of interactive enzyme systems to the inhibitor which was subjected to the sterilizing environment; and
   c) detecting the activity of the plurality of interactive enzyme systems to determine the microorganism survivability of the sterilizing environment.

18. A two-step biological process for determining the effectiveness of a sterilization procedure comprising the steps of:
   a) placing a test indicator containing one or more components, but not all of the components of a plurality of interactive enzyme systems and a sample of microorganisms into a sterilization chamber;
   b) performing the sterilization procedure within the chamber;
   c) removing the test indicator from the chamber;
   d) adding the remaining components of the plurality of interactive enzyme systems to the one or more components in the test indicator to form a mixture and adding a fluid media to the sample of microorganisms to form a culture;
   e) incubating the mixture for a first period of time sufficient for detecting the presence or absence of a detectable product to make a first-step determination of the effectiveness of the sterilization procedure; and
   f) incubating the culture for a second period of time sufficient for detecting the presence or absence of a metabolic product of growth to make a second-step determination of the effectiveness of the sterilization procedure.

19. The process of claim 18 wherein the sample of microorganisms comprises a population of spores of the genus Bacillus, Neurospora, Candida, or Clostridium.

20. The process of claim 18 wherein the first incubation period is less than about one minute and the second incubation period is less than about one hour.

21. A test indicator for determining the effectiveness of a sterilization procedure comprising:
   a) a container having liquid impermeable and substantially gas non-absorptive walls; and
   b) at least one opening in the container walls leading into a chamber which contains at least two enzymes of a plurality of interactive enzyme systems with a gas-transmissive barrier between the at least two enzymes and the at least one opening.

22. The test indicator of claim 21 wherein the barrier is selected from the group consisting of Gortex membranes, polymer membranes, sponges, stoppers and compartmentalized disks.

23. The test indicator of claim 22 wherein the solid support is selected from the group consisting of celluloses, plastics, glasses, ceramics, polymer membranes, polymers, and combinations thereof.

24. The test indicator of claim 22 wherein the solid support is a highly compartmented cellulosic disk suspended in an anhydrous medium.

25. The test indicator of claim 21 wherein the at least two enzymes of the plurality of interactive enzyme systems are coimmobilized on a solid support.

26. A self-contained test indicator for determining the effectiveness of a sterilization procedure comprising:
   a) an outer container having liquid impermeable and substantially gas non-absorptive walls and at least one opening covered with a gas-transmissive cover, said at least one opening leading into a chamber that contains a first and a second vial wherein;
   b) the first vial has at least one opening which is covered with a gas-transmissive cover and contains at least one component but not all of the component of a plurality of interactive enzyme systems; and
   c) the second vial contains the remaining components of the plurality of interactive enzyme systems which when mixed with the at least one component of the first vial produces a detectable product wherein;
   d) said vials are constructed of a material which can be opened and their contents mixed without being removed from the test indicator.

27. A biological process for determining the effectiveness of a sterilization procedure comprising the steps of:
   a) placing a test indicator containing one or more component, but not all of the components of a plurality of interactive enzyme systems into a sterilization chamber;
   b) performing the sterilization procedure within the chamber;
   c) adding the remaining components of the plurality of interactive enzyme systems to the one or more components in the test indicator to form a mixture;
   d) incubating the mixture for less than one minute; and
   e) detecting the presence or absence of a product.

28. A biological process for determining the effectiveness of a sterilization procedure comprising the steps of:
   a) placing a test indicator containing one or more components but not all of the components of a plurality of interactive enzyme systems into a sterilization chamber;
   b) performing the sterilization procedure within the chamber;
   c) adding the remaining components of the plurality of interactive enzyme systems to the one or more components in the test indicator; and
   d) detecting the presence or absence of a product.

29. A test kit for determining the effectiveness of a sterilization procedure comprising:
   a) a first container having liquid impermeable and substantially gas non-absorptive walls that is to be subjected to a sterilizing environment;
   b) at least one opening in the container leading into a chamber which contains at least two components, but not all the components, of a plurality of interactive enzyme systems, with a gas-transmissive barrier between the at least two components and the at least one opening; and c) a second container containing the remaining components of the plurality of interactive enzyme systems which are to be added to the at least two or more components that are subjected to the sterilizing environment.

* * * * *